United States Patent [19]

Moon, Jr. et al.

[11] Patent Number: 4,622,846
[45] Date of Patent: Nov. 18, 1986

[54] CONSISTENCY AND STATIC GEL STRENGTH MEASURING DEVICE AND METHOD

[75] Inventors: John J. Moon, Jr.; Jim B. Surjaatmadja; Mark C. Ehlert, all of Duncan, Okla.

[73] Assignee: Halliburton Company, Duncan, Okla.

[21] Appl. No.: 795,290

[22] Filed: Nov. 5, 1985

[51] Int. Cl.[4] ........................................... G01N 11/14
[52] U.S. Cl. ......................................... 73/59; 73/64.1
[58] Field of Search ................................... 73/59, 64.1

[56] References Cited

U.S. PATENT DOCUMENTS

| | | | |
|---|---|---|---|
| 2,096,222 | 10/1937 | Bock | 265/11 |
| 2,122,765 | 7/1938 | Weiler | 265/11 |
| 2,266,733 | 12/1941 | Bays et al. | 265/11 |
| 2,273,750 | 2/1942 | Clagett, Jr. | 265/11 |
| 2,409,014 | 10/1946 | Bohmer et al. | 73/54 |
| 2,435,416 | 2/1948 | Thomson et al. | 18/8 |
| 2,603,087 | 7/1952 | Von Hortenau | 73/59 |
| 2,626,786 | 1/1953 | McGlothlin | 259/8 |
| 2,630,706 | 3/1953 | Maxon | 73/54 |
| 2,683,984 | 7/1954 | Boyle et al. | 73/59 |
| 2,821,079 | 1/1958 | Kerridge | 73/54 |
| 2,904,401 | 9/1959 | Booth | 23/188 |
| 3,027,756 | 4/1962 | Head | 73/53 |
| 3,269,171 | 8/1966 | Bruss et al. | 73/60 |
| 3,285,057 | 11/1966 | De Zurik | 73/59 |
| 3,347,089 | 10/1967 | Perry | 73/59 |
| 3,402,729 | 9/1968 | Richmond et al. | 137/92 |
| 3,407,618 | 10/1968 | Mullins, Jr. | 62/136 |
| 3,636,753 | 1/1972 | Thiele et al. | 73/59 |
| 3,751,975 | 8/1973 | Katsura | 73/59 |
| 3,803,903 | 4/1974 | Lin | 73/59 |
| 3,875,791 | 4/1975 | Fitzgerald et al. | 73/59 |
| 4,044,602 | 8/1977 | Higgs et al. | 73/59 |
| 4,157,036 | 6/1979 | Kivenson | 73/290 |
| 4,175,425 | 11/1979 | Brookfield | 73/59 |
| 4,181,023 | 1/1980 | Clamroth et al. | 73/432 |
| 4,283,938 | 8/1981 | Epper et al. | 73/59 |
| 4,299,118 | 11/1981 | Gau et al. | 73/59 |
| 4,466,276 | 8/1984 | Ruyak et al. | 73/59 |
| 4,484,468 | 11/1984 | Gau et al. | 73/60 |

FOREIGN PATENT DOCUMENTS 12829  9/1972  Japan ...................................... 73/64.1

OTHER PUBLICATIONS

SPE 9285 "Transition Time of Cement Slurries Between the Fluid and Set State" p. 3897, vol. 41, Halliburton Services Sales and Service Catalog.
"Description of Stirring Chamber," Halliburton Services.
"Oil Well Cement Testing Equipment—Atmospheric Pressure Consistometer", Chandler Engineering Company.

Primary Examiner—Stewart J. Levy
Assistant Examiner—Joseph W. Roskos
Attorney, Agent, or Firm—James R. Duzan; E. Harrison Gilbert, III

[57] ABSTRACT

An appartus and method for testing characteristics of a substance, such as a cement slurry to be used within an oil or gas well, are provided. The apparatus includes a single drive motor which can be actuated in either a dynamic mode or a static mode to measure, in the preferred embodiment, either consistency or static gel strength of the substance. A single display is switchably connectible to one of two scaling circuits which scale a single transducer output signal to provide the desired measurement.

20 Claims, 9 Drawing Figures

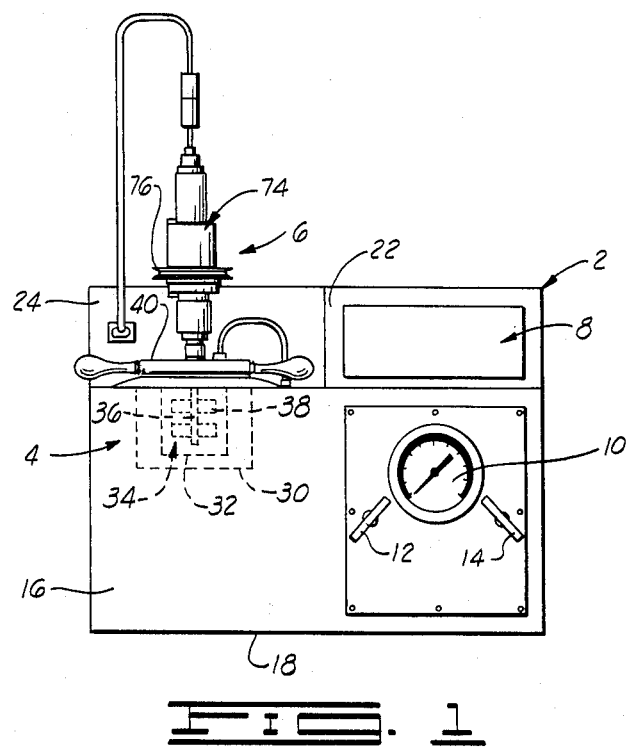
FIG. 1
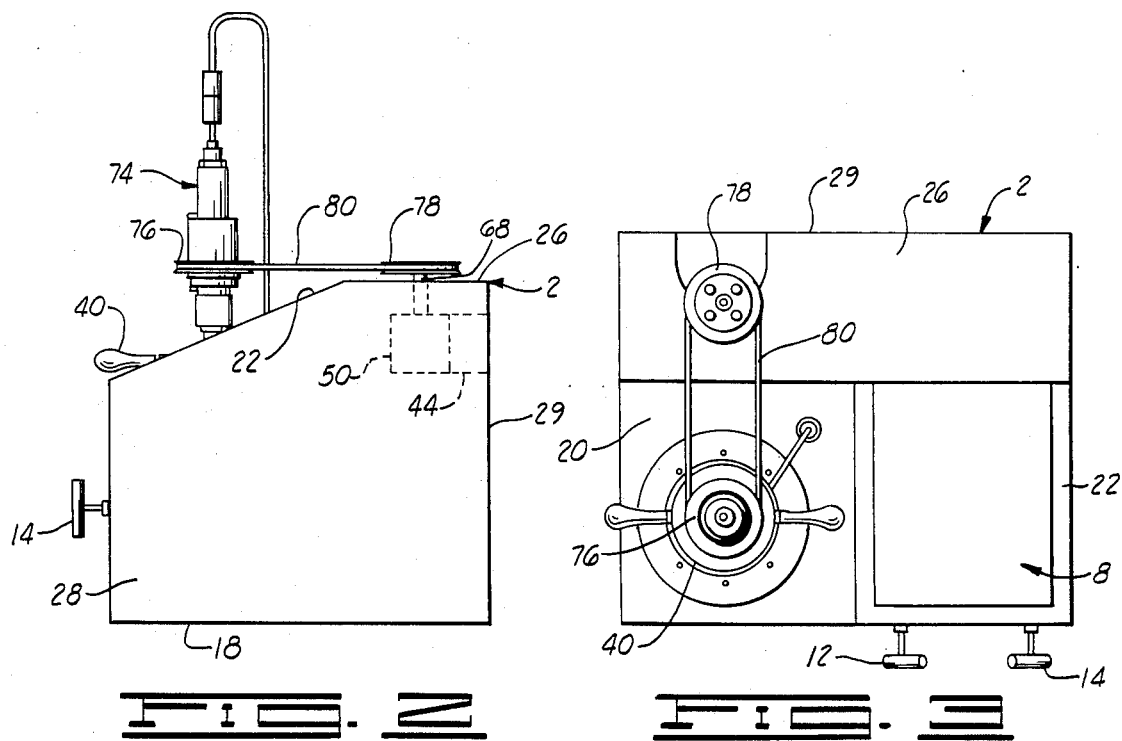
FIG. 2
FIG. 3

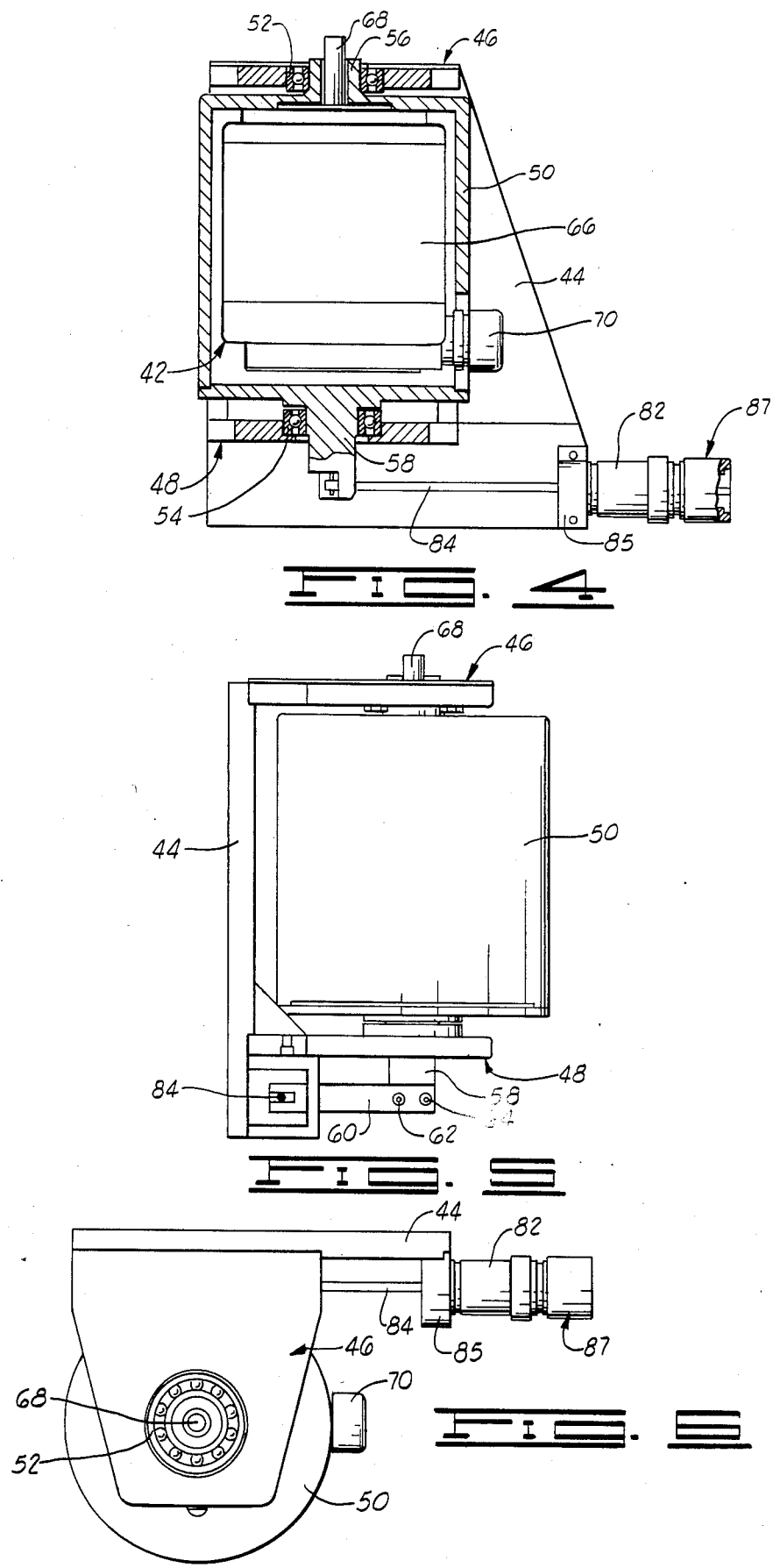

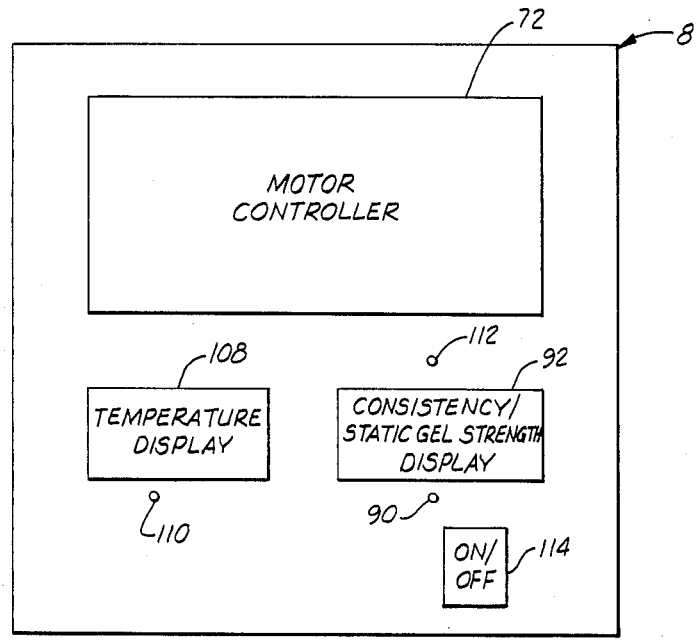
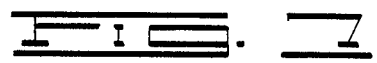
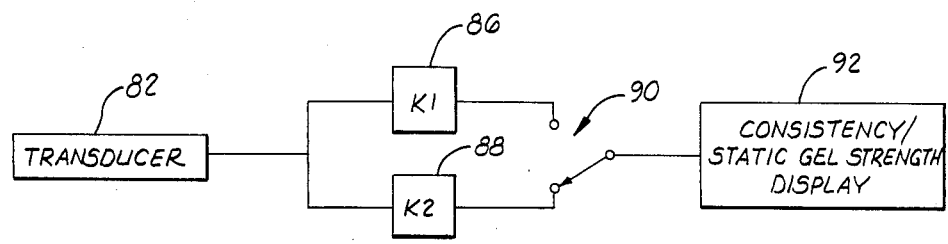
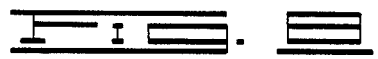
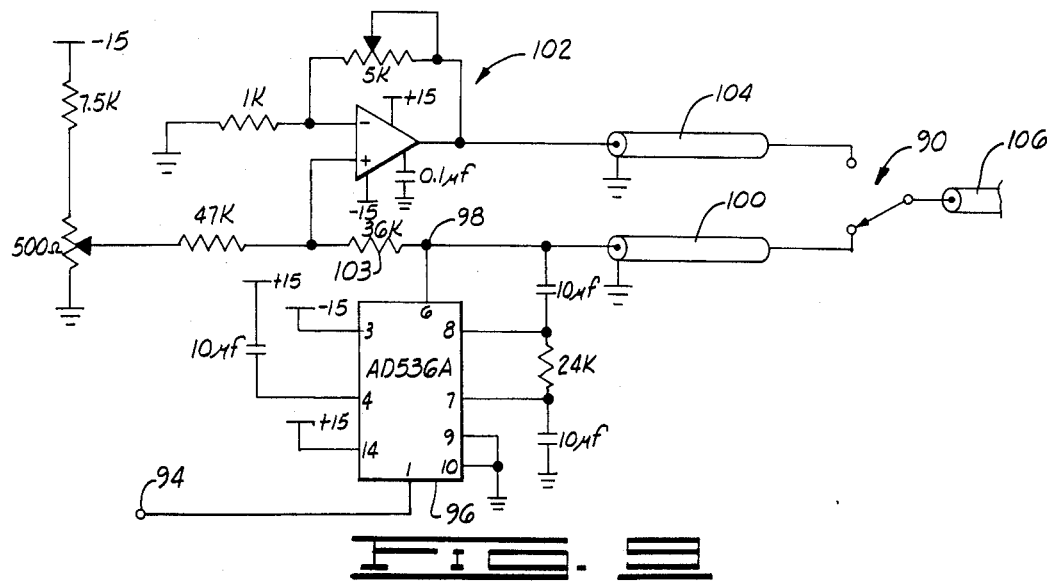

CONSISTENCY AND STATIC GEL STRENGTH MEASURING DEVICE AND METHOD

BACKGROUND OF THE INVENTION

This invention relates generally to apparatus and methods for testing characteristics of a substance and more particularly, but not by way of limitation, to apparatus and methods for measuring the consistency and static gel strength of a cement slurry.

In the oil and gas industry, different fluids are used for various purposes in drilling and completing a well. For example, batches of cement must be made and pumped into the well for cementing the casing into the well bore. The cement is generally pumped through the casing for flow back up the annulus between the well casing and the well bore to create the necessary bond.

Because different batches of fluids can have different characteristics which affect how the fluids perform in the high temperature and high pressure environments found downhole, there is the need for equipment which can perform different tests on a fluid sample prior to the fluid being pumped downhole so that one can determine if that particular batch of fluid has the proper characteristics for the particular situation. For example, with respect to a cement slurry, the consistency and static gel strength of a particular blend are important characteristics to know. The consistency is important because it indicates the flowability of the cement slurry. The static gel strength is important because it relates to the ability of the cement to prevent gas leaks when the cement is flowed into the annulus. If the cement will not properly gel, gas may create channels through the cement to the surface causing a hazardous situation. The static gel strength also relates to the ability of the cement to flow, which indicates how long the cement slurry can be pumped.

The importance of obtaining the aforementioned two characteristics of a cement slurry are well known in the art. Various types of single-function test apparatus by which one or the other of the aforementioned characteristics can be measured are known. Multi-function apparatus have also been proposed or developed wherein separate drive equipment and often separate displays are used for separately operating on a container holding the substance to be tested. However, we are not aware of a single, compact apparatus by which both consistency and static gel strength can be measured utilizing one and only one drive element so that the apparatus can be constructed more compactly and cost effectively. To further enhance the compactness and cost effectiveness of such a needed apparatus, such apparatus should include a single display and means by which either one or the other of the tested characteristics can be displayed since only one test would be conducted at any one time, thereby obviating the need for duplicate displays. Of course, such an apparatus should also have the heating and pressurizing abilities of known types of test equipment. It is also desirable that such an apparatus should have the capability of being controlled by a suitable computer, such as a microprocessor-based device. A corresponding novel method of efficiently testing a substance for these characteristics is also needed.

SUMMARY OF THE INVENTION

The present invention meets the aforementioned needs by providing a novel and improved apparatus and method for testing multiple characteristics of a substance, particularly consistency and static gel strength of a cement slurry in the preferred embodiment. The apparatus of the present invention is relatively compact and cost efficient in that it utilizes only a single drive motor to obtain the wide range of rotational speeds needed to accommodate both types of tests. It also incorporates only one display for displaying the test results. The apparatus also includes heating and pressurizing elements to place the substance under test at desired operating conditions. It is also contemplated that the present invention can be readily adapted for control by a computer of a suitable type, such as a microcomputer.

Broadly, the apparatus of the present invention comprises receptacle means for receiving a substance, which receptacle means has a stationary member and a rotatable member disposed in rotative connection with the stationary member; one and only one drive means for rotating the rotatable member relative to the stationary member so that the rotatable member acts on the substance at a selectable one of a first speed, at which a first one of the characteristics is determined, and a second speed, at which a second one of the characteristics is determined; and sensing means for sensing a responsive force acting through the rotatable member and the drive means when the drive means rotates the rotatable member and for converting the responsive force into a measurement signal corresponding to a respective one of a measurement of the first one of the characteristics when the drive means rotates the rotatable member at the first speed and a measurement of the second one of the characteristics when the drive means rotates the rotatable member at the second speed. The apparatus also comprises one and only one display means, responsive to the sensing means, for selectably displaying one of the measurements of the first and second ones of the characteristics.

The method of the present invention comprises placing the substance to be tested in a container; rotating a paddle in the container at a selectable speed, including: connecting one and only one motor to the paddle; and selectively actuating the motor so that the motor rotates the paddle at a speed within one of a first speed range and a second speed range, wherein the first speed range is defined in the preferred embodiment as a consistency speed range including a speed of 150 revolutions/minute and wherein the second speed range is defined in the preferred embodiment as a static gel strength speed range including a speed of 0.5 degree/minute; detecting a torque imposed on the motor in response to the step of rotating; and converting the detected torque into a consistency measurement when the motor is actuated in the first speed range and into a static gel strength measurement when the motor is actuated in the second speed range. The method further comprises displaying through one and only one display the consistency measurement when the motor is acutated in the first speed range and the static gel strength measurement when the motor is actuated in the second speed range.

Therefore, from the foregoing, it is a general object of the present invention to provide a novel and improved apparatus and method for testing characteristics of a substance. Other and further objects, features and advantages of the present invention will be readily apparent to those skilled in the art when the following description of the preferred embodiment is read in conjunction with the accompanying drawings.

BRIEF DESCRIPTION OF THE DRAWINGS

FIG. 1 is a front elevational view of an apparatus constructed in accordance with the preferred embodiment of the present invention.

FIG. 2 is a side elevational view of the apparatus shown in FIG. 1.

FIG. 3 is a plan view of the apparatus shown in FIG. 1.

FIG. 4 is a partial sectional elevational view of a single motor and its mounting structure used in the preferred embodiment.

FIG. 5 is another elevational view of the assembly shown in FIG. 4.

FIG. 6 is a plan view of the assembly shown in FIG. 4.

FIG. 7 is a block diagram of a control panel of the apparatus shown in FIG. 1.

FIG. 8 is a block diagram of a portion of a sensing means interfaced with a single display used in the preferred embodiment.

FIG. 9 is a schematic circuit diagram of the preferred embodiment of the scaling circuits, $K_1$ and $K_2$, and the switch shown in FIG. 8.

DETAILED DESCRIPTION OF THE PREFERRED EMBODIMENT

With reference initially to FIGS. 1-3, the preferred embodiment of the apparatus of the present invention will be described. FIGS. 4-9 will be subsequently referred to during the more particular description of specific elements of the preferred embodiment. It is to be noted that the preferred embodiment is described with reference to measuring the consistency and static gel strength of a cement slurry; however, the concepts of the present invention can be adapted for use in measuring other characteristics, such as viscosity, of other types of substances.

As shown in FIGS. 1-3, the preferred embodiment of the apparatus of the present invention broadly includes a housing 2 to which is connected receptacle means 4 for receiving the substance, such as the exemplary cement slurry, to be tested. The apparatus includes one and only one drive means 6 for rotating a rotatable member of the receptacle means 4 so that the rotatable member acts on the substance at a selectable one of two speeds. In the preferred embodiment the two speeds are significantly different whereby in previous apparatus known to us the two different speeds were obtained by two different drive mechanisms. The preferred embodiment apparatus also includes sensing means (more particularly identified hereinbelow) for sensing a responsive or reactive force acting through the rotatable member and the drive means 6 when the drive means 6 rotates the rotatable member and for converting the responsive or reactive force into a measurement signal indicating a respective one of the measurements corresponding to the speed at which the drive means is rotating the rotatable member. Control of the drive means 6 and display of the measurement is made via a control and display panel 8, the details of which are not shown in FIGS. 1-3 for purposes of simplicity but which are more particularly shown in FIG. 7 (it is also contemplated that control could be effected through a serial communication from a computer, for example). FIG. 1-3 also show that the preferred embodiment apparatus includes a pressure gauge 10, which responds to pressure within the receptacle means 4 as known to the art, disposed in the housing 2 adjacent control handles 12, 14 of high pressure valves forming parts of a conduit system contained within the housing 2. The conduit system is not shown in the drawings because it is of any suitable type readily known to the art for conducting fluids to and from the receptacle means 4 in manners as known to the art.

The housing 2 of the preferred embodiment is a relatively compact structure having height, width and depth dimensions of not greater than approximately twenty-five inches. As shown in FIGS. 1-3, the housing 2 includes a vertical front panel 16 extending upwardly from a bottom panel 18 to a horizontal shelf panel 20, in which the receptacle means 4 is disposed, and to an angular panel 22, in which the control and display panel 8 is disposed. The panel 20 extends from the front panel 16 to an intermediate vertical panel 24. The panel 24 extends vertically to a horizontal top panel 26 which is spaced above the front panel 16 and to which the angular panel 22 obliquely extends from the front panel 16. Similar side panels, one of which is identified by the reference numeral 28 shown in FIG. 2, enclose the ends of the housing 2. A back panel 29 completes the enclosure of the housing 2. The panels of the housing 2, as well as the other parts of the preferred embodiment of the present invention, are made of suitable materials known to the art.

The receptacle means 4 connected to the shelf panel 20 of the housing 2 is defined in the preferred embodiment by a suitable autoclave designed to accept an API standard testing can or container in which an API standard paddle can be rotatively received or connected; however, it is contemplated that the present invention can be utilized without such an API can or paddle. The autoclave has an internal spiral cooling jacket used to circulate water during rapid cool-down cycles, and it also has a high pressure port in the bottom used for safe evacuation of cement samples; both of these features are of types as known to the art and will thus not be more particularly described and are not shown in the drawings for purposes of simplicity.

The autoclave is schematically depicted in FIG. 1 and identified by the reference numeral 30. The testing container within the autoclave 30, and into which the sample of cement slurry is to be placed prior to conducting a test, is also schematically depicted in FIG. 1 as identified by reference numeral 32. In the preferred embodiment the container 32 is maintained stationary within the autoclave 30. Rotatably disposed within the stationary container 32 is a paddle 34 schematically shown in FIG. 1. The paddle 34 has a central, vertically extending support shaft 36 from which suitable paddle members or blades 38 extend in a manner as known to the art. The shaft 36 is connected to the drive means 6 through a lid 40 of the autoclave 30 as more particularly described hereinbelow.

The drive means 6 includes a single motor 42 which in the preferred embodiment is a variable speed stepper motor, such as a Compumotor M series motor/drive Model M106-120 providing 25,000 steps/revolutions from which the preferred embodiment speed range of approximately 0.5 degree/minute (i.e., 1/720 rpm) to approximately 200 revolutions/minute is obtained. FIGS. 2 and 4-6 show that the motor 42 is connected to the back panel 29 of the housing 2, beneath the top panel 26, by means of a support member 44 connected to the back panel 29. Extending perpendicularly from the support member 44 toward the intermediate vertical panel 24 are an upper bearing cover member 46 and a lower bearing cover member 48 vertically spaced from each other a sufficient distance to receive a motor enclosure 50 therebetween. The motor enclosure 50 is journaled between the members 46, 48 in an upper bearing 52 and a lower bearing 54 suitably retained within their respective cover members 46, 48. The motor enclosure 50 has a substantially cylindrical shape with axially extending neck portions 56, 58 received in the bearings 52, 54 so that the enclosure 50 can pivot or rotate about its central vertical axis as viewed in FIG. 4, for example. Extending radially outwardly from the neck portion 58 is a transducer loading arm 60, which is connected to the neck portion 58 by suitable means such as screws 62, 64.

Coaxially retained within a hollow interior of the enclosure 50 is the motor 42. The motor 42 includes an outer casing forming part of a stator portion 66 within which a rotor portion is rotatively disposed. The stator portion 66 is fixed to the enclosure 50 so that movement of the stator portion 66 is coupled to the journaled enclosure 50. Forming part of the rotor portion of the motor 42 is a drive shaft 68 extending through a bore formed through the neck portion 56 of the enclosure 50 and up through a hole in the top panel 26 in parallel relationship to the support shaft 36 of the paddle 34. A connector 70 extends radially from the stator portion 66 of the motor 42 for mechanically and electrically connecting with a suitable control cable extending from a suitable motor control means for controlling the speed of rotation of the motor 42.

The motor control means of the preferred embodiment is identified in FIG. 7 by the reference numeral 72 shown therein disposed in the control and display panel 8. In the preferred embodiment the motor control means 72 is a Compumotor Model 2100 indexer having an RS-232 single cable interface; however, it is contemplated that other suitable motor control means can be used, such as a suitably programmed microcomputer connected through a similar RS-232 single cable interface. In the preferred embodiment the motor control means 72 selectably actuates the motor 42 so that the drive shaft 68 rotates at a selectable one of two speeds, which speeds for the preferred embodiment are within the rotational speed range of approximately 0.5 degree/minute to approximately 200 revolutions/minute. More broadly, the motor control means 72 selectably rotates the motor 42 either at a rotational speed less than approximately 1 degree/minute so that the response of a reactive torque arising therefrom is proportional to the static gel strength of the substance being tested within the autoclave 30 or at a rotational speed greater than approximately 100 revolutions/minute (e.g., at a speed of 150 revolutions/minute) so that the responsive or reactive torque arising therefrom is proportional to the consistency of the substance. In the preferred embodiment the specific speed is selected pursuant to API guidelines for the particular test performed.

To transfer the rotational force from the drive shaft 68 to the paddle 34, the drive means 6 includes a suitable connector means for rotatably coupling these two devices. In the preferred embodiment, this connector means includes a suitable magnetic drive mechanism 74 of a type as known to the art. The mechanism 74 includes an axial member (not shown) connected to the support shaft 36 of the paddle 34. This axial member is magnetically coupled to an outer portion including a sheave 76. The sheave 76 is connected to a sheave 78, affixed to the drive shaft 68, by means of an endless drive belt 80 as shown in FIGS. 1-3. Therefore, when the motor control means 72 actuates the motor 42, the drive shaft 68 rotates the paddle 34 through the mechanical and magnetic coupling provided by the elements 74, 76, 78, 80. As the drive shaft 68 rotates relative to the stator portion 66 of the motor 42, a responsive or reactive torque is transmitted back through the magnetic and mechanical coupling members to the stator 66 and thus to the motor enclosure 50 and the transducer loading arm 60 which are fixed relative to the stator 66.

Such responsive or reactive torque is sensed by the sensing means which in the preferred embodiment includes a transducer 82. The transducer 82 has an input connected to the transducer loading arm 60 by means of a transducer loading rod 84 (FIGS. 4-6). The transducer 82 has an output connected to circuit means 86, 88 (FIGS. 8 and 9) through which an electrical signal, provided through the transducer output in response to the detected torque transmitted thereto through the rod 84, is conditioned to correspond to a consistency measurement or a static gel strength measurement. One of these measurements is numerically displayed, as selected by a switch 90, through a single display 92 contained within the control and display panel 8.

In the preferred embodiment the transducer 82 is a precision linearly variable differential transformer (LVDT) force transducer of a type as known to the art. As shown in FIGS. 4 and 6, the LVDT transducer is supported by a transducer support bracket 85 connected to the support member 44. An overload stop and protective cap member 87 associated with the transducer 82 is also shown in FIGS. 4 and 6. The transducer loading rod 84 interacts with the LVDT so that the LVDT provides an electrical signal corresponding to the reactive torque arising from the interaction between the paddle 34 and the substance within the container 32. The transducer output is connected to the circuits 86, 88, which in the preferred embodiment are scaling circuits, the preferred embodiments of which are shown in FIG. 9.

As shown in FIG. 9, the output of the transducer 82 is connected to a terminal 94. The transducer output signal applied to the terminal 94 is scaled by a signal averaging circuit 96, such as of the specific type identified in FIG. 9 for providing a voltage proportional to the rms value of the analog transducer output signal. The output of the circuit 96 is connected to a junction 98. The junction 98 constitutes the output of the circuit 86, which output junction is connected to one terminal of the switch 90 through a coaxial cable 100. The circuit 88 includes the aforementioned circuit 96 as well as an amplifier network 102 connected to the junction 98 through a resistor 103 as shown in FIG. 9. The network 102 further conditions the signal to provide an output signal corresponding to static gel strength units. This output signal is connected through a coaxial cable 104 to another terminal of the switch 90. The pole of the switch 90 is connected by a coaxial cable 106 to the display 92. Therefore, the circuits 86, 88 convert the signal from the transducer 82 into a measurement signal corresponding to consistency or static gel strength, depending upon the speed at which the motor 42 is operating, which measurement signal is connected through the switch 90 to the display 92. The switch 90 is set in accordance with the speed at which the motor 42 is operated by the motor control means 72 so that the static gel strength measurement is numerically indicated in the display 92 when the motor 42 is operating within the slower static gel strength speed range and so that the consistency measurement is numerically indicated in the display 92 when the motor 42 is operating within the higher consistency speed range.

The display 92 is any suitable type of device for numerically displaying the selected one of the consistency measurement signal or the static gel strength measurement signal. The display 92 is only a single display device having just the appropriate number of digits to alternatively display either the consistency or static gel strength. Only one display 92 is used to reduce the number of parts utilized in the present invention over those used in at least some other multi-function test apparatus.

Accompanying the display 92 in the control and display panel 8 is a temperature display 108 for displaying a sensed temperature of the substance when the substance is received in the container 32. This temperature is obtained through suitable temperature sensing devices disposed within the slurry or within a wall of the container 32 in manners as known to the art. A switch 110 accompanies the temperature display 108 to select between either the slurry or wall temperature.

FIG. 7 also shows that the panel 8 includes a speed range select switch 112 by which the motor control means 72 can be easily switched between the static gel strength speed and the consistency speed once the motor control means 72 has been preset. The panel 8 also includes a master on/off switch 114.

Control of the preferred embodiment is readily obtained through operation of the switches contained on the control and display panel 8. Manual control is provided in the preferred embodiment by means of manipulation of the control devices in the motor control means 72. Once the motor control means 72 has been preset, a consistency or a static gel strength test is selected by appropriately manipulating the switch 112 once the on/off switch 114 has been turned on. Because the consistency test is conducted while rotating the paddle 34 at a relatively high rotational speed so that the substance is agitated, selection of this test via the switch 112 can be said to operate the device in a dynamic mode; whereas operation of the device to conduct a static gel strength test can be said to be a static mode of operation because the paddle 34 is rotated at a relatively slow rotational speed so that the tested substance is not agitated but is allowed to remain "static." So that the display 92 will correspond to the test selected via the switch 112, the switch 90 must also be manually set in the appropriate position to display consistency when the switch 112 is controlling the motor control means 72 to drive the motor 42 at the preselected consistency speed or to display static gel strength when the switch 112 is positioned to control the motor control means 72 to drive the motor 42 at the preselected static gel strength speed. Although manual control is provided in the preferred embodiment, it is contemplated that the preferred embodiment can be readily adapted for computerized control with the output signals of temperature, pressure, consistency and static gel strength being made available for data acquisition by the computer.

As desired, pressure and heat can be applied to the autoclave 30 in manners as known to the art to condition the cement slurry similarly to the environment in which it is anticipated the tested blend will be ultimately used. In the preferred embodiment, the apparatus 30 can be controlled to heat the cement slurry in the autoclave to a temperature of up to 600° F. and it can pressurize the substance up to a pressure of 20,000 lbs/square inch. Such heating and pressurizing is accomplished after the substance is placed in the container 32 in a manner as known to the art.

With the substance placed in the container 32 and preconditioned to a desired temperature and pressure, the motor control means 72 is then activated through the switch 112 whereby the paddle 34 is rotated in the container 32 at the selected speed preset into the motor control means 72. In the preferred embodiment the preselected speed for a consistency test is within a range including a speed of 150 revolutions/minute, and the preselected speed for a static gel strength test is within a range including a speed of 0.5 degree/minute.

As the paddle 34 rotates, it interacts with the cement slurry whereby a responsive or reactive torque is imposed on the paddle 34, which reactive torque is proportional to or in correspondence with the consistency or static gel strength of the cement slurry. This torque is transmitted back through the magnetic coupling mechanism 74 and the mechanical coupling mechanism including the belt 80 to the motor 42. This reactive torque acts through the stator portion 66 connected to the motor enclosure 50 so that the transducer loading arm 60 moves the transducer loading rod 84. Movement of the rod 84 activates the transducer 82 to provide an electrical signal to the circuits 86, 88.

The circuits 86, 88 respectively convert the electrical signal from the transducer 82 into a corresponding scaled electrical signal representing a consistency measurement and a static gel strength measurement. The one of these measurement signals selected by the switch 90, which selection is in correspondence with the setting of the switch 112, is displayed in the single display 92. In the preferred embodiment, the conversion effected by the circuits 86, 88 is effectively a scaling by a suitable factor ($K_1$ or $K_2$) of the input signal into an output signal indicative of the respective consistency or static gel strength units to be displayed.

Thus, the present invention is well adapted to carry out the objects and attain the ends and advantages mentioned above as well as those inherent therein. While a preferred embodiment of the invention has been described for the purpose of this disclosure, numerous changes in the construction and arrangement of parts and the performance of steps can be made by those skilled in the art, which changes are encompassed within the spirit of this invention as defined by the appended claims.

What is claimed is:

1. An appartus for measuring at least two characteristics of a substance, comprising:
   receptacle means for receiving the substance, said receptacle means having a stationary member and a rotatable member disposed in rotative connection with said stationary member;
   one and only one drive means for rotating said rotatable member relative to said stationary member so that said rotatable member acts on the substance at a selectable one of a first speed, at which a first one of the at least two characteristics is determined, and a second speed, at which a second one of the at least two characteristics is determined; and sensing means for sensing a responsive force acting through said rotatable member and said drive means when said drive means rotates said rotatable member and for converting said responsive force into a measurement signal corresponding to a respective one of a measurement of the first one of the characteristics when said drive means rotates said rotatable member at the first speed and a measurement of the second one of the characteristics when said drive means rotates said rotatable member at the second speed.

2. An apparatus as defined in claim 1, further comprising one and only one display means, responsive to said sensing means, for selectably displaying one of the measurements of the first and second ones of the characteristics.

3. An apparatus as defined in claim 2, wherein said sensing means includes:
   a transducer responsive to movement of said drive means;
   first scaling circuit means, connected to said transducer, for scaling an output from said transducer to define the measurement signal corresponding to the first one of the characteristics;
   second scaling circuit means, connected to said transducer, for scaling the output from said transducer to define the measurement signal corresponding to the second one of the characteristics; and
   switch means for selectably connecting one of said first and second scaling circuit means to said display means.

4. An apparatus as defined in claim 1, wherein said drive means includes:
   a single electrical stepper motor having a rotor connected to said rotatable member and having a stator relative to which said rotor rotates; and
   motor control means for selectably actuating said motor so that said rotor rotates at a selectable one of the first and second speeds, which speeds are within the rotational speed range of approximately 0.5 degree/minute to approximately 200 revolutions/minute.

5. An apparatus as defined in claim 4, wherein said sensing means includes a linearly variable differential transformer means for generating an electrical signal in response to movement of said stator of said motor.

6. An apparatus as defined in claim 5, wherein:
   said sensing means further includes:
      first circuit means for converting said electrical signal into a first scaled electrical signal representing a measurement of consistency of the substance; and
      second circuit means for converting said electrical signal into a second scaled electrical signal representing a measurement of static gel strength of the substance; and
   said apparatus further comprises means, responsive to a selectable one of said first and second scaled electrical signals, for numerically displaying the selected one of the consistency measurement and the static gel strength measurement.

7. An apparatus as defined in claim 1, wherein:
   said first and second speeds are within the range between approximately 0.5 degree/minute and approximately 200 revolutions/minute; and
   said sensing means includes:
      transducer means for generating an electrical signal in response to a responsive torque transmitted through said drive means;
      first circuit means for converting said electrical signal into a first scaled electrical signal representing a measurement of consistency of the substance when said drive means rotates said rotatable member at said first speed; and
      second circuit means for converting said electrical signal into a second scaled electrical signal representing a measurement of static gel strength of the substance when said drive means rotates said rotatable member at said second speed.

8. An apparatus for measuring consistency and static gel strength of a substance, comprising:
   a housing;
   a container connected to said housing for receiving the substance;
   a paddle rotatively disposed in said container;
   a single motor connected to said housing, said motor having a rotor and a stator;
   connector means for connecting said rotor and said paddle;
   sensing means for sensing responsive torque arising from said motor rotating said paddle through the substance when the substance is received in said container; and
   motor control means for rotating said rotor of said motor at a selectable one of a rotational speed less than approximately 1 degree/minute so that the reponsive torque arising therefrom is proportional to static gel strength of the substance and a rotational speed greater than approximately 100 revolutions/minute so that the responsive torque arising therefrom is proportional to consistency of the substance.

9. An apparatus as defined in claim 8, further comprising:
   a support member connected to said housing;
   an upper bearing cover member extending from said support member;
   a lower bearing cover member extending from said support member and spaced from said upper bearing cover member;
   an upper bearing retained in said upper bearing cover member;
   a lower bearing retained in said lower bearing cover member; and
   a motor enclosure journaled in said upper and lower bearings, said enclosure having said motor retained therein and having a transducer loading arm extending therefrom.

10. An apparatus as defined in claim 9, wherein said sensing means includes:
   transducer means for generating an electrical signal in response to a responsive torque transmitted through said motor enclosure;
   first circuit means for converting said electrical signal into a first scaled electrical signal representing a measurement of consistency of the substance; and
   second circuit means for converting said electrical signal into a second scaled electrical signal representing a measurement of static gel strength of the substance.

11. An apparatus as defined in claim 10, further comprising a single numeric display mounted in said housing for alternatively responding to a selectable one of said first and second scaled electrical signals so that only one of the consistency and static gel strength measurements is displayed at a time.

12. An apparatus as defined in claim 8, wherein:
said housing includes a vertical front panel, a horizontal top panel spaced above said front panel, a horizontal shelf panel extending from said front panel and having said container connected thereto, and an angular panel extending obliquely between said front panel and said top panel;
said paddle has a vertically extending support shaft when said paddle is disposed in said container;
said motor includes a stator, connected beneath said top panel so that movement of the stator about the axis of rotation of said motor is transmitted to said sensing means, and a rotor, having a drive shaft extending through said top panel parallel to said support shaft of said paddle; and
said connector means includes means for rotatively coupling said drive shaft and said support shaft.

13. An apparatus as defined in claim 12, further comprising a control and display panel retained in said angular panel, said control and display panel having said motor control means connected thereto and including single measurement display means for alternatively numerically displaying a selectable one of the measured consistency and static gel strength of the substance.

14. An apparatus as defined in claim 13, wherein:
said control and dislay panel further includes temperature display means for displaying a sensed temperature of the substance when the substance is received in said container; and
said apparatus further comprises a pressure gauge, responsive to a pressure within said container, mounted in said front panel.

15. An apparatus as defined in claim 12, further comprising:
a support member connected below said top panel;
an upper bearing cover member extending from said support member;
a lower bearing cover member extending from said support member and spaced from said upper bearing cover member;
an upper bearing retained in said upper bearing cover member;
a lower bearing retained in said lower bearing cover member; and
a motor enclosure journaled in said upper and lower bearings, said enclosure having said stator connected thereto and having a transducer loading arm extending therefrom.

16. An apparatus as defined in claim 15, wherein said sensing means includes:
a linearly variable differential transformer; and
a transducer loading rod connected between said transducer loading arm and said linearly variable differential transformer.

17. A method of measuring consistency and static gel strength of a substance, comprising:
placing the substance in a container;
rotating a paddle in the container at a selectable speed, including:
connecting one and only one motor to the paddle; and
selectively actuating the motor so that the motor rotates the paddle at a speed within one of a first speed range and a second speed range, wherein the first speed range is defined as a consistency speed range including a speed of 150 revolutions/minute and wherein the second speed range is defined as a static gel strength speed range including a speed of 0.5 degree/minute;
detecting a torque imposed on the motor in response to said step of rotating; and
converting the detected torque into a consistency measurement when the motor is actuated in the first speed range and into a static gel strength measurement when the motor is actuated in the second speed range.

18. A method as defined in claim 17, further comprising displaying through one and only one display the consistency measurement when the motor is actuated in the first speed range and the static gel strength measurement when the motor is actuated in the second speed range.

19. A method as defined in claim 17, wherein:
said step of detecting includes connecting a transducer to the motor so that the transducer provides an electrical signal in response to the torque imposed on the motor; and
said step of converting includes:
scaling the electrical signal by a first factor to provide a first scaled electrical signal corresponding to the consistency measurement; and
scaling the electrical signal by a second factor to provide a second scaled electrical signal corresponding to the static gel strength measurement.

20. A method as defined in claim 19, further comprising actuating a display with a selectable one of the first and second scaled electrical signals.

* * * * *